United States Patent [19]

Hara

[11] 4,094,322

[45] June 13, 1978

[54] THERAPEUTICAL APPARATUS USING ELECTRIC FIELD

[75] Inventor: Katsumasa Hara, Tokyo, Japan

[73] Assignee: Hakuju Institute for Health Science Co., Ltd., Tokyo, Japan

[21] Appl. No.: 697,365

[22] Filed: Jun. 18, 1976

[51] Int. Cl.² .............................................. A61N 1/40
[52] U.S. Cl. .................. 128/419 N; 128/413
[58] Field of Search ............... 128/419 N, 420 R, 190, 128/404, 405, 413, 191 A, 1 G, 362, 373, 376, 377, 378, 303.13, 303.14, 303.17, 303.18, 303.19, 422, 2.06 F

[56] References Cited

U.S. PATENT DOCUMENTS

| 399,084 | 3/1889 | Schmalz et al. ................ 128/376 |
| 796,791 | 8/1905 | Anderson ........................ 128/376 X |
| 1,279,120 | 9/1918 | Kellogg ........................... 128/377 |
| 3,750,672 | 8/1973 | Berckheim ...................... 128/376 |
| 3,938,507 | 2/1975 | Sarnoff et al. ................. 128/2.06 F |

FOREIGN PATENT DOCUMENTS

| 973,081 | 9/1950 | France ............................. 128/191 A |
| 919,338 | 2/1963 | United Kingdom ............ 128/419 N |

*Primary Examiner*—William E. Kamm
*Attorney, Agent, or Firm*—Larson, Taylor and Hinds

[57] ABSTRACT

A therapeutical apparatus using electric field comprising a main electrode vertically arranged at the head side of mat on which a patient lies or accommodated in a housing arranged at the head side of a bed on which the patient lies. A further electrode fixedly or movably arranged at the foot side of the mat or the bed, insulating cords connected with the electrodes, respectively, so as to enable voltage to be applied to the electrodes, a checking point arranged adjacent to the main electrode and including a conductive plate, and a detecting means arranged between the conductive plate and the main electrode and rendered operative when the checking point is touched by his finger of the patient.

4 Claims, 18 Drawing Figures

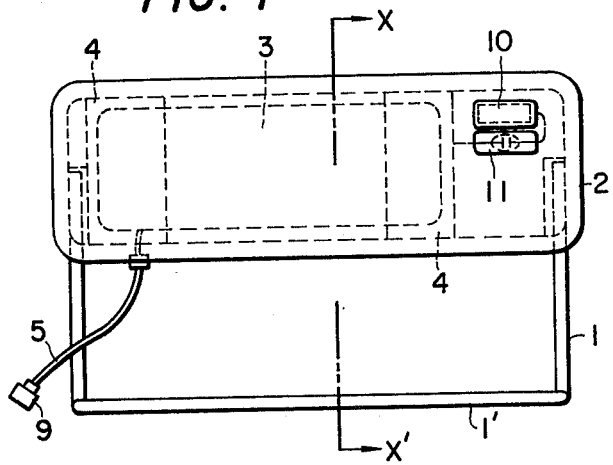
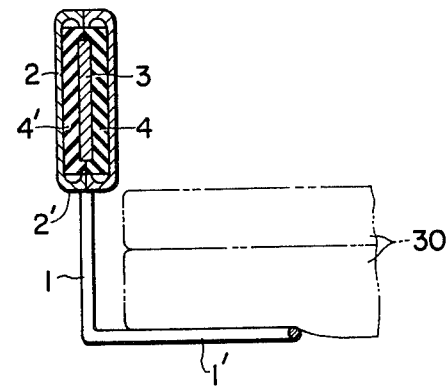
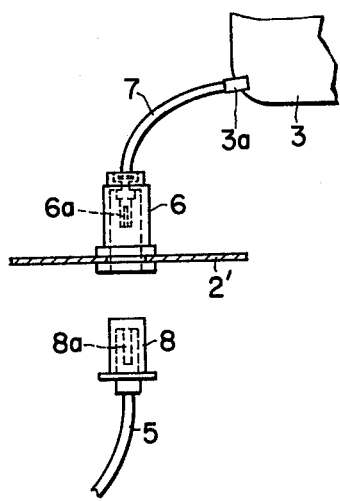
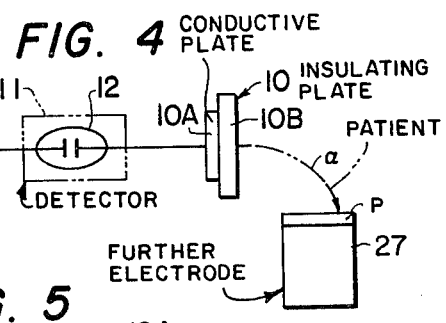
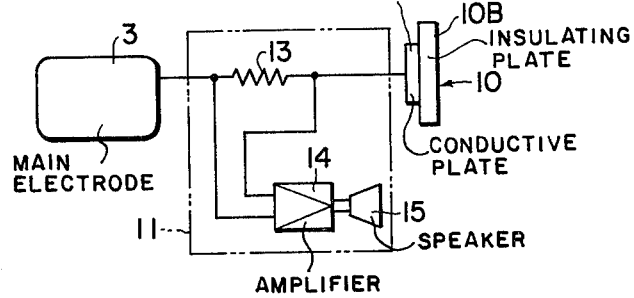
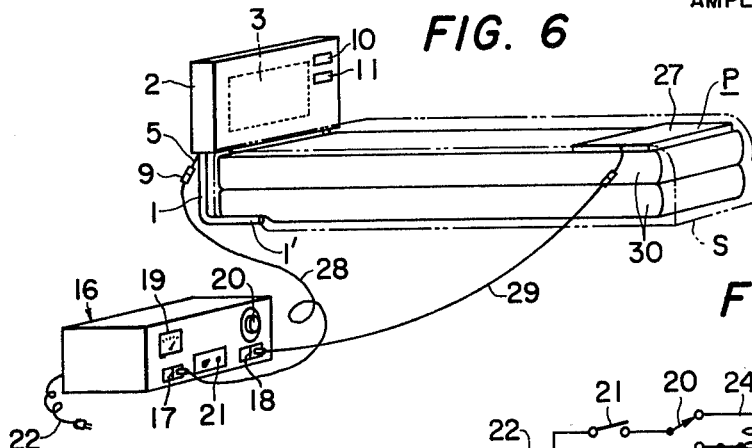
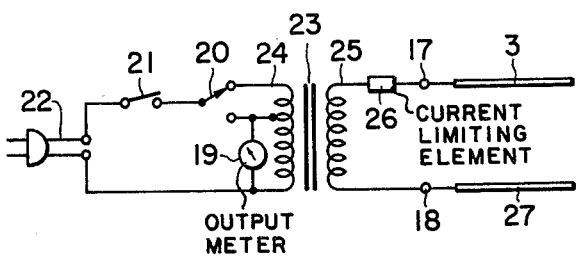

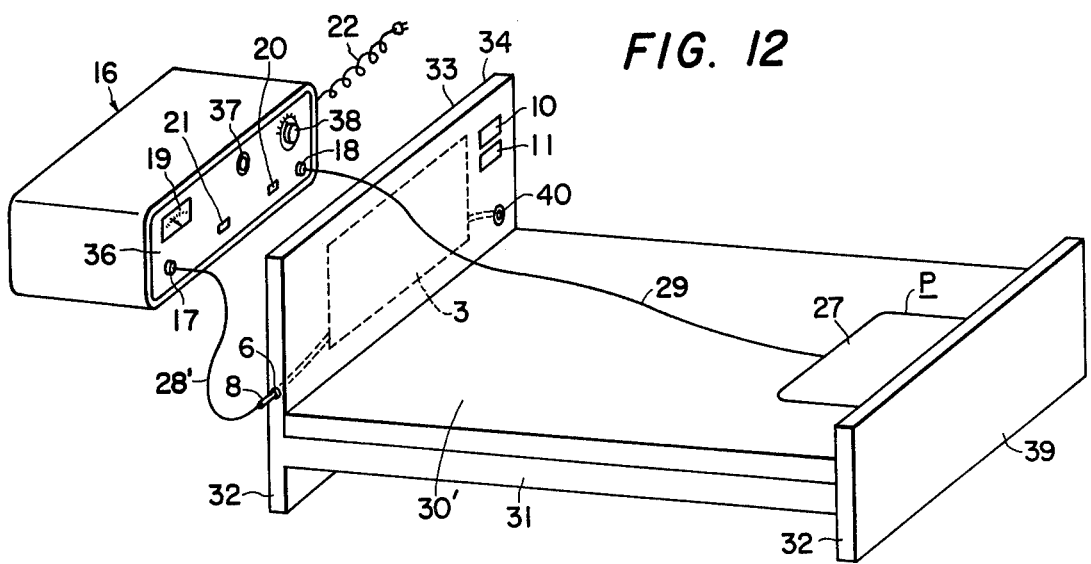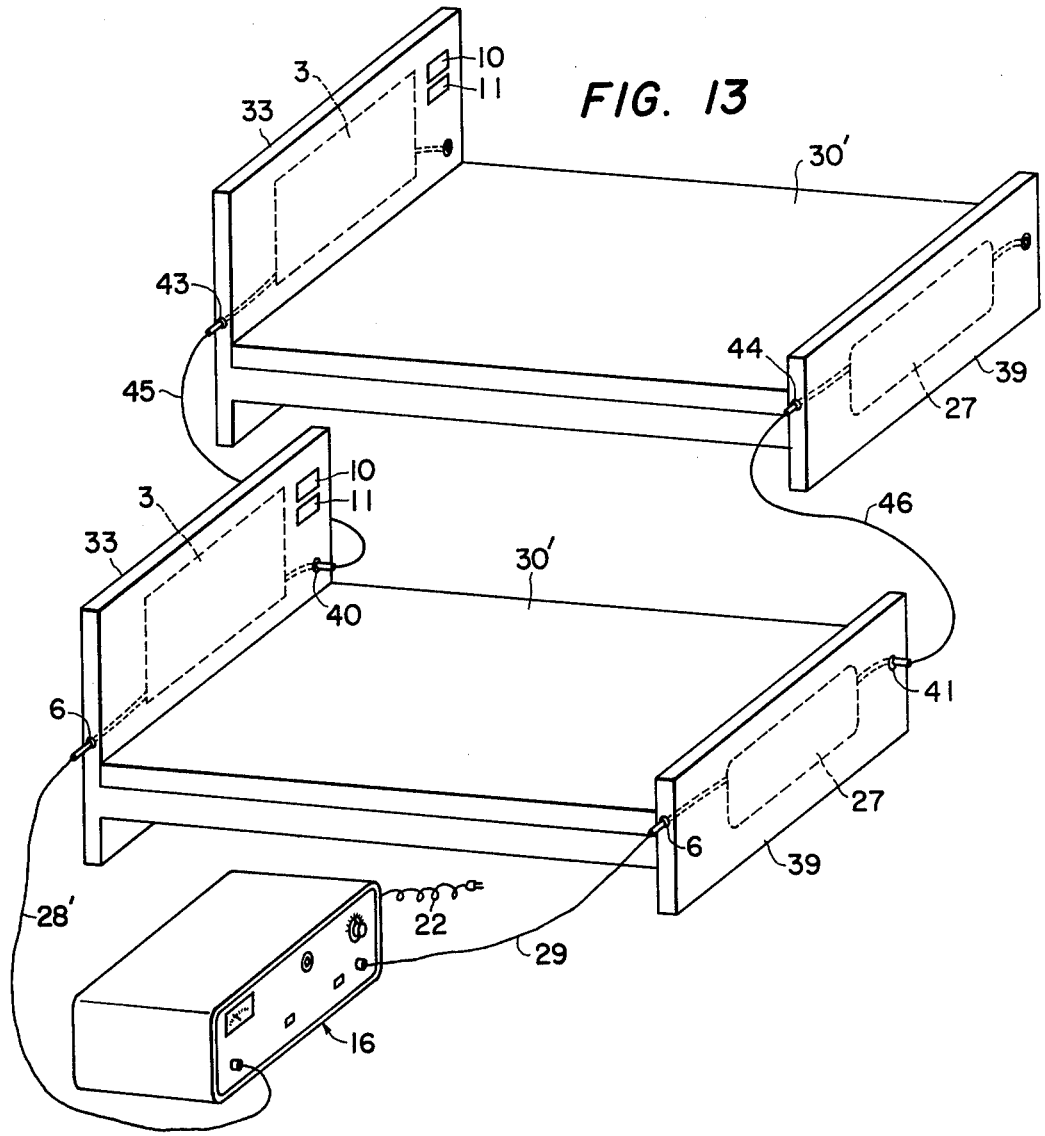

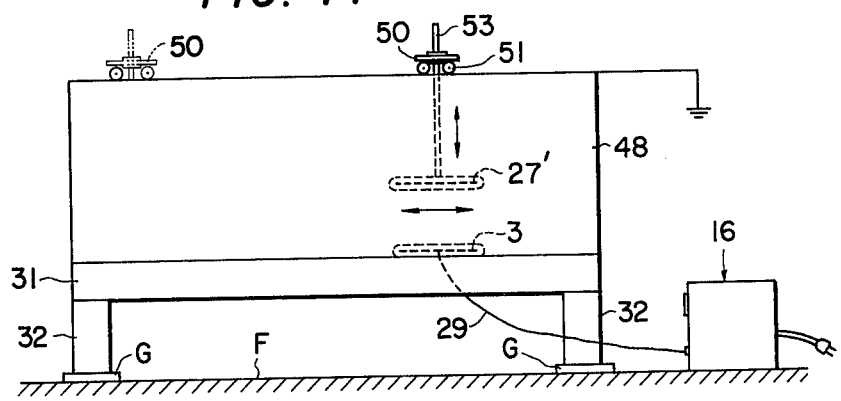
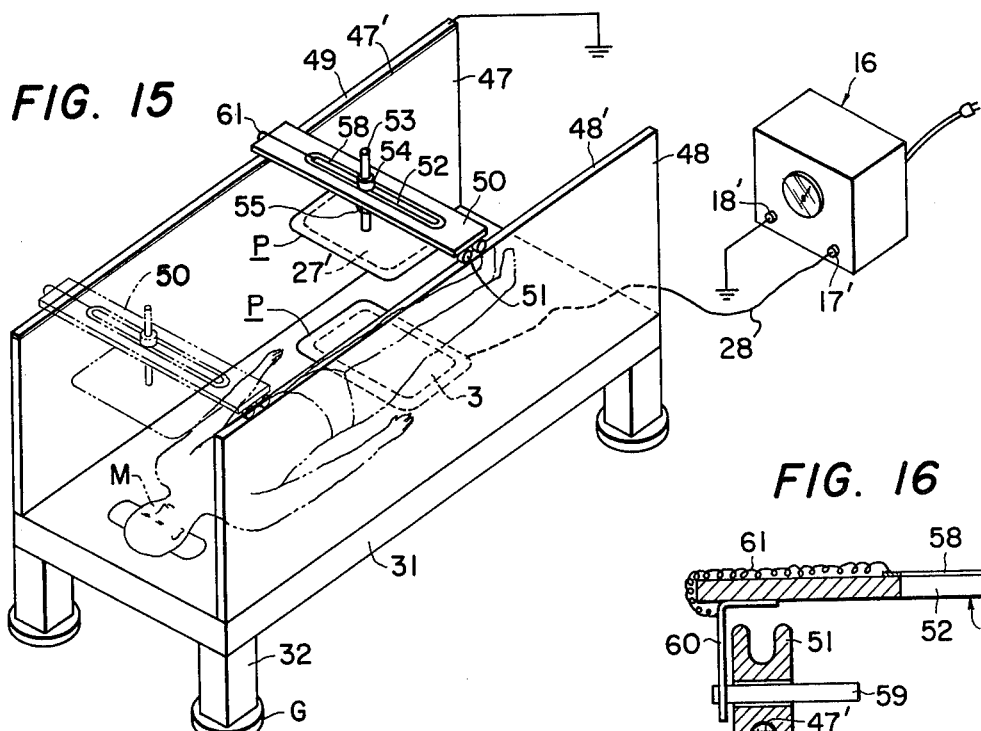
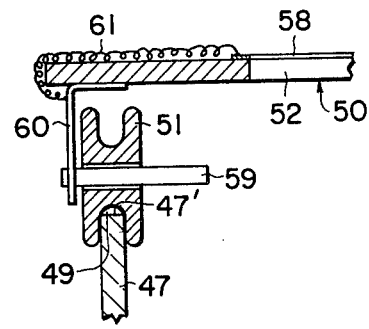
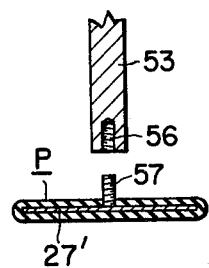
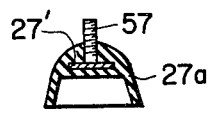

THERAPEUTICAL APPARATUS USING ELECTRIC FIELD

The present invention relates to therapeutical apparatus which can be easily and safely used by a patient in his home and, more particularly, a therapeutical apparatus which comprises a main electrode arranged at the head side of mat or a bed on which the patient lies, a further electrode arranged at the foot side of the mat or the bed, and a voltage generating means connected with each of the electrodes.

BACKGROUND OF THE INVENTION

As a therapeutical treatment applying voltage to a human body, there has been well known the one using electric field, in which voltage is applied to a main electrode and a further electrode so as to treat the human body in the electric field formed between both of the electrodes. This therapeutical treatment is based on the well-known principle that the human body electrically charged in the electric field of high voltage is caused to have a certain change in the internal organs or systems and a remarkable change in the ions contained in the blood to thereby increase calcium ions and to decrease magnesium phosphorous in the blood.

It is also well known that an unhealthy body is deficient in the amount of calcium ions and has a surplus of magnesium and phosphorous.

Accordingly, the therapeutical treatment as mentioned above is intended to give a favorable effect to the unhealthy body by electrically charging the body in the electric field of high voltage and to cure a variety of sicknesses by refreshing the cells of the body.

However, the treatment using high voltage requires special knowledge and technique as to electrical insulation and can be performed only in a big hospital or institute where persons skilled in the field and the equipment necessary for the treatment are ready. There has not been developed such apparatus as enables a person to receive the treatment in their home, but as the effectiveness attained by the treatment becomes better known to the public, the demand for an apparatus which can be easily used has been increased.

SUMMARY OF THE INVENTION

It is, therefore, a primary object of the present invention to provide an apparatus which enables the therapeutical treatment using an AC or AC and DC superimposed electric field to be easily and safely received in home.

Another object of the present invention is to provide a therapeutical apparatus using an AC or AC and DC superimposed electric field which can be safely used by a patient himself who has no special knowledge in the field.

A further object of the present invention is to provide a therapeutical apparatus wherein electrodes are arranged to be freely movable and to be applicable to a mat on which the patient lies.

A still further object of the present invention is to provide an apparatus wherein each of the electrodes is incorporated in a bed.

A still further object of the present invention is to provide an apparatus which enables the treatment using electric field such as described above to be received at the time when the patient sleeps on the mat or the bed or at any other time when he wants.

A still further object of the present invention is to provide an apparatus of which safety can be ckecked up by the patient himself.

A still further object of the present invention is to provide an apparatus which enables a desired part of the patient's body to receive the treatment.

These and other objects as well as the merits of the present invention will be apparent from the following detailed description with reference to the accompanying drawings.

It may be understood that any variations and modifications of the mechanism are included in the scope and spirit of the claims and specification of the present invention.

BRIEF DESCRIPTION OF THE DRAWINGS

FIG. 1 is a front view showing an electrode of screen shape according to the present invention;

FIG. 2 is a section taken along the line X—X' in FIG. 1;

FIG. 3 is a view showing how an insulating cord is connected with the electrode shown in FIG. 1;

FIGS. 4 and 5 are views showing a checking point and a detecting means;

FIG. 6 is an isometric view showing how an embodiment of the present invention is used;

FIG. 7 is a circuit diagram of the embodiment shown in FIG. 6;

FIG. 12 is an isometric view showing a further embodiment of the present invention;

FIG. 13 is an isometric view showing how two beds incorporating the embodiment shown in FIG. 8 are connected with each other;

FIG. 14 is a front view showing a still further embodiment of the present invention;

FIG. 15 is an isometric view of the embodiment shown in FIG. 14;

FIG. 16 is an enlarged view showing the portion at which a moving element and one of wall plates shown in FIG. 15 are engaged with each other;

FIG. 17 is a partial section showing how a supporting rod and an earth electrode employed in the embodiment shown in FIG. 14, 15 are engaged with each other; and FIG. 18 is a section showing another example of the earth electrode.

DETAILED DESCRIPTION OF THE PREFERRED EMBODIMENTS

Figure 8:
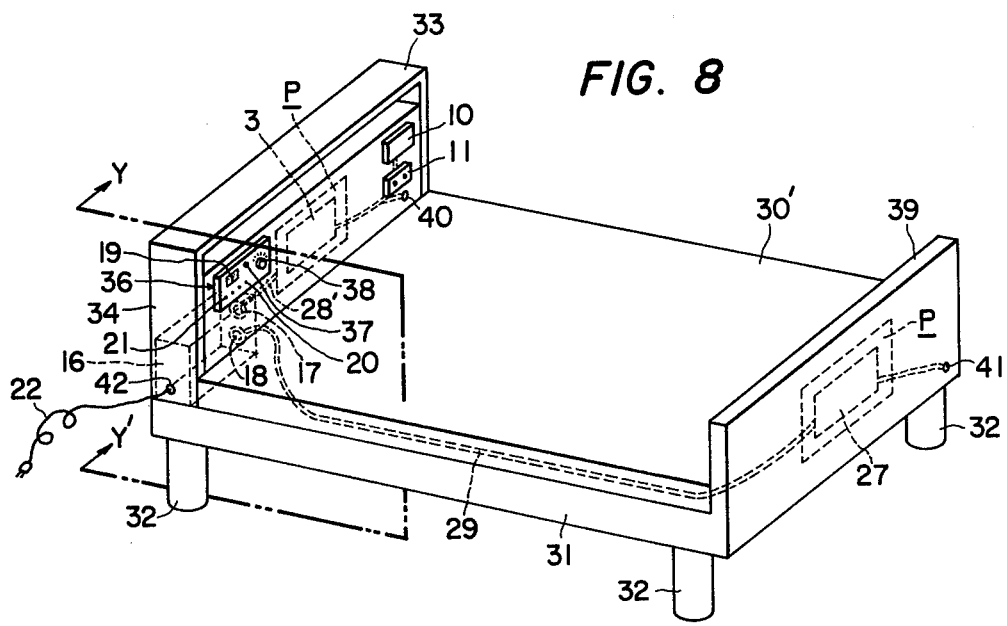
FIG. 8 is an isometric view showing another embodiment of the present invention.

There will be now described an embodiment of the present invention with reference to the accompanying drawings.

In FIG. 1, numeral 1 represents a supporting frame of "L" shape and 2 a casing which is attached to the top of the supporting frame 1 and in which a main electrode 3 is housed and covered by supporting plates 4, 4' made of insulating material (see FIG. 2).

Numeral 5 denotes an insulating cord intended to apply voltage to the main electrode 3 and the connection between the main electrode 3 and the insulating cord 5 is as shown in FIG. 3. Namely, the insulating cord 5 is easily connected with the main electrode 3 in such a manner that a connector 6a in a female connector 6 fixedly attached to the base plate 2' of the casing 2 and connected with a terminal 3a of the main electrode 3 through an insulating cord 7 is brought into engagement with a connector 8a in a male connector 8 attached to an end of the insulating cord 5.

Numeral 9 represents a connector attached to the other end of the insulating cord 5, said connector 9 being connected with an output terminal 17 of a high voltage generating device 16 which will be described later.

In FIG. 4, numeral 10 represents a checking point or monitoring means connected with the main electrode 3 and when a patient touches this checking point 10, for example, by his finger, a detecting means 11 is rendered operative to tell the patient that voltage is being applied to the main electrode 3.

To further described the checking point 10, it comprises a conductive plate 10A and an insulating plate 10B attached to the front face of the conductive plate 10A, which is connected with the main electrode 3 through a neon tube 12 which is used as the detecting means 11 in the example shown in FIG. 4. The conductive plate 10A is connected with a further electrode 27 as shown by the broken line a in FIG. 4 representing the patient and when the patient lies on the bed with a part of his body, for example, his feet being contacted with the electrode 27 and then touches the checking point 10 by his finger, a circuit combining the main electrode 3 with the electrode 27 through his body is established by means of the capacitive connection between checking point 10 and electrode 27. Therefore, the neon tube 12 is turned on when voltage is being applied to the main electrode 3 while the neon tube 12 is left in the "OFF" condition when voltage is not being applied to the main electrode 3 to thereby allow any trouble in, for example, the insulating cords to be detected. The insulating plate 10B is intended to reduce the shock which the patient feels when he touches the checking point 10 by his finger.

The other example shown in FIG. 5 uses sound instead of light, in which a resistance 13 is inserted instead of the neon tube 12 and the voltage generated across the resistance 13 is amplified by an amplifier 14 to sound a speaker 15 when the patient touches the checking point 10 by his finger.

FIG. 6 shows how the therapeutical apparatus of the present invention is used. In the Figure numeral 16 represents a device for generating a high AC voltage or a high voltage in which AC and DC voltages are superposed, and in the front panel of said device are provided output terminals 17 and 18, an output meter 19, a voltage regulator 20 and a power source switch 21. Numeral 22 represents a cord connected with a power source.

FIG. 7 shows an example of the circuit (of AC type) of the therapeutical apparatus shown in FIG. 6. In the Figure numeral 23 denotes a boosting transformer and it is so designed that the commercial power source is connected with a primary winding 24 to which an output meter 19 is connected, while an optional voltage, for example, of 3,000 V is generated at the side of a secondary winding 25. Numeral 26 represents a current controlling element such as condenser and resistance, and said element serves to limit flow of current by its impedance value, thus surely protecting the patient from any danger. Numeral 27 represents a further electrode located oposite to the main electrode 3 so that an electric field is formed therebetween. The main electrode 3 is connected with the output terminal 17 of the high voltage generating device 16 through an insulating cord 28 while the further electrode 27 with the output terminal 18 of the high voltage generating device 16 through an insulating cord 29.

Referring to FIG. 6 again, the horizontal portion 1' of the supporting frame 1 is fixedly inserted under mats 30 on which the patient lies with his head adjacent to the casing 2. The electrode 27 covered by insulating material P is placed on the mats 30 at which the feet of the patient are located, and then the mats 30 are wholly covered by a sheet S as shown by the broken line in FIG. 6. The electrodes 3 and 27 are connected with the high voltage generating device 16 through the insulating cords 28 and 29, respectively. The electrode 27 may be a conductive metal plate covered by a sheet of synthetic resin, or a conductive carbon plate covered by a sheet of synthetic resin, or a conductive fiber cloth covered by a sheet of synthetic resin.

After the patient lies on the mats 30 to locate himself between the electrodes 3 and 27, he touches the checking point 10 by his finger to see if the detecting means 11 is operated or not. When it is operated, he can receive the therapeutical treatment using the electric field formed between the electrodes while he is lying or sleeping on the mat.

In the embodiment of the present invention the casing 2 housing the main electrode 3 and supported by the supporting frame 1 is arranged to be a so-called screen. Therefore, the apparatus can be removed in a place when not used to thereby make it unnecessary to always fix the apparatus in a place. In other words the apparatus can be brought out to be used with the horizontal portion 1' of the supporting frame 1 being inserted under the mats 30 whenever the patient wants. Further, this embodiment of the present invention is provided with the checking point 10, which is arranged to render the detecting means 11 operative or to leave the detecting means 11 nonoperated when touched by his finger of the patient depending on whether voltage is being applied to each of the electrodes. Accordingly, when the detecting means 11 is not operated, it can be easily found that trouble is present in, for example, one of the insulating cords.

Figure 9:
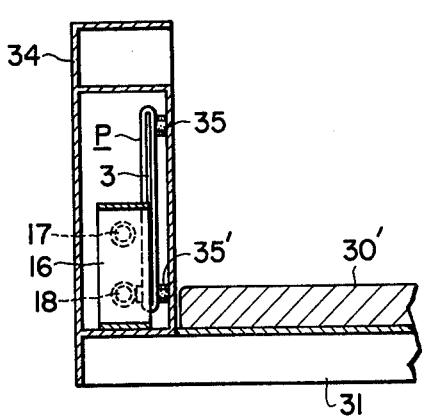
FIG. 9 is a section taken along the line Y—Y' in FIG. 8.

FIG. 8 shows another embodiment of the present invention. Numeral 31 represents a base of the bed, to which are attached four legs 32 and on which is mounted at mat 30' made of insulating resilient material such as polyurethane and rubber. Numeral 33 represents a main electrode portion, which is arranged at the side of the bed where his head is located when the patient lies on the bed. As shown in FIGS. 8 and 9, the main electrode 33 comprises fixing a main electrode 3 in a housing 34 through insulating supporting members 35 and 35', said main electrode 3 being completely covered by insulating material P such as plastic. In the housing 34 is provided the high voltage generating device 16 having output terminals 17 and 18. To the inner face of the main electrode portion 33 is attached a control panel 36 in which are provided the power source switch 21, a pilot lamp 37, the output meter 19, the voltage regulator 20 and a time switch 38. The output terminal 17 of the voltage generating device 16 is connected with the main electrode 3 through a cord 28'. To the inner face of the housing 34 are further attached the checking point 10 and the detecting means 11.

Figure 10:
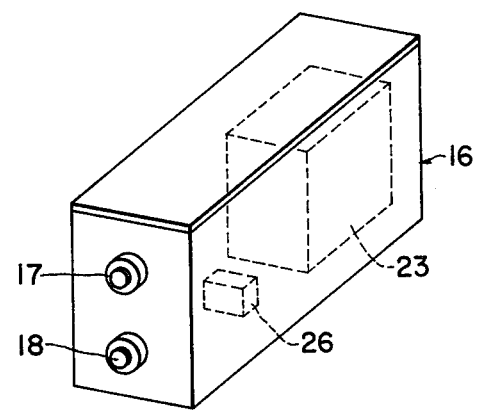
FIG. 10 is an isometric view showing a voltage generating device employed in the embodiment shown in FIG. 8.

FIG. 10 is an isometric view of the high voltage generating device 16 employed in the embodiment of the present invention shown in FIG. 8. The device 16 contains the boosting transformer 23 and the current controlling element 26 such as condenser and resistance.

Referring to FIG. 8 again, in a foot side plate 39 opposite to the main electrode portion 33 is embedded the further electrode 27 in insulated fashion, said electrode 27 being connected with the output terminal 18 of the high voltage generating device 16 through the insulating cord 29. Numerals 40 and 41 represent additive plug sockets which are provided in the main electrode portion 33 and in the side plate 39, respectively, and which are to be used to supply voltage to another bed.

Figure 11:
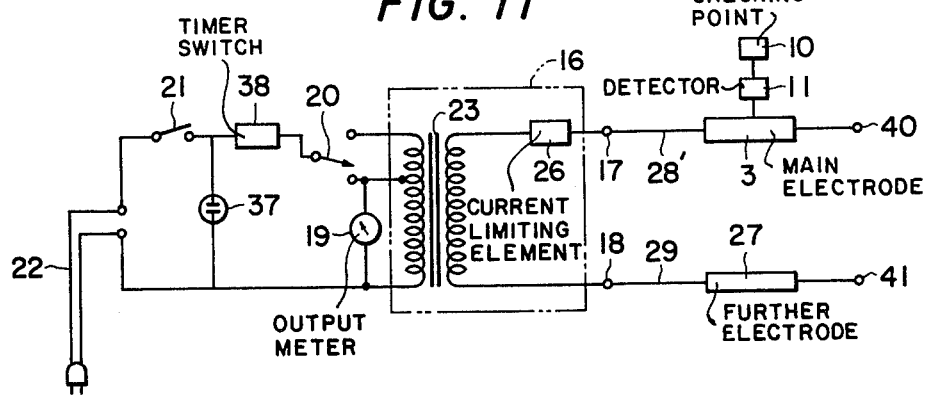
FIG. 11 is a circuit diagram of the embodiment shown in FIG. 8.

FIG. 11 is a circuit diagram of the apparatus shown in FIG. 8. The power source switch 21 is turned on and the voltage regulator 20 is then operated to apply a voltage desired to the electrodes 3 and 27. It can be easily found by touching the checking point 10 by his of the patient whether the voltage is being applied to the electrodes. The patient lies on the insulating mat 30' in the electric field formed between the main electrode 3 and the further electrode 27, thus allowing the therapeutical treatment using the electric field to be applied to the patient. In FIG. 11, an output meter 19 is connected to the primary winding of transformer 23. A pilot lamp 37 and a timer switch 38 are also connected on the primary side.

FIG. 12 shows a still another embodiment of the present invention, which is different from the one shown in FIG. 8 in that the high voltage generating device 16 and the control panel 36 are separated from the bed and that the corresponding electrode 27 is not embedded in the foot side plate 39 but placed on the mat 30' after it is covered by insulating material P.

The embodiment shown in FIG. 12 enables the further electrode 27 to be moved on the mat 30' according to the height of the patient and the housing 34 to be made thinner than that of the embodiment shown in FIG. 8.

FIG. 13 shows two beds in which the additive plug sockets 40 and 41 are connected with plug sockets 43 and 44 through insulating cords 45 and 46, respectively, so as to enable the therapeutical treatment to be applied to two patients simultaneously.

FIGS. 14 and 15 show a still another embodiment of the present invention by which a desired part of the patient lying on the bed can receive the therapeutical treatment using an electric field. The base of the bed is supported by the legs 32, each of which is insulated by an insulating seat G from the floor F. Numerals 47 and 48 represent wall plates vertically extending from both sides of the base 31 and parallel to each other. To the top 47' of the wall plate 47 is attached a conductive rail 49 made of copper plate or the like. Numeral 50 represents a moving element, at both ends of which are provided a pair of grooved wheels 51, respectively, said wheels 51 being mounted on the tops 47' and 48' of the wall plates 47 and 48. As shown in FIGS. 16 and 17 there is provided in the moving element 50 a slot 52 through which a supporting rod 53 made of conductive material passes. The outer and central portion of the supporting rod 53 is threaded and to this threaded portion of the rod 53 are screwed a nut 54 from the upper side of the moving element 50 and a nut 55 from the underside of the moving element 50 so as to fix the supporting rod 53 at an optional position of the slit 52. In the lower end of the supporting rod 53 is provided a tapped hole 56, into which a screw 57 attached to a further, ground or earth electrode 27' is fitted, said ground electrode 27' being covered by insulating material P at the outer circumference thereof as shown in FIG. 17. Numeral 58 denotes a conductive bar enclosing the slot 52 of the moving element 50. The grooved wheels 51, shafts 59 and a supporting member 60 of reversed "L" shape attached to the shafts 59 comprise a conductor and the supporting member 60 and the conductive bar 58 are connected with each other through a conductive line 61 as shown in FIG. 16. Since the supporting rod 53 is also a conductor as stated above, the moving element 50 can be slid in the longitudinal direction of the bed always keeping the earth electrode 27' contacted with the rail 49. Numeral 3 denotes the main electrode of high voltage, of which outer circumference is covered by insulating material P. This main electrode 3 is connected through the insulating cord 28 with an output terminal 17' of the device 16 for generating a high AC voltage or a high voltage in which AC and DC voltages are superimposed. The earth electrode 27' is earthed through the wall plate 47 directly to ground (see FIG. 15).

The patient lies on the base 31 of the bed and the main electrode 3 of high voltage is located under a part of the body M of the patient who is to receive the treatment. The moving element 50 is then slid in the longitudinal direction of the bed to a position corresponding to the main electrode 3. The nuts 54 and 55 are then adjusted to determine the height of the earth electrode 27' from the bed. And then, the high voltage generating device 16 is switched to an "ON" condition. As a result, only that diseased part of the body M is securely held in the electric field to receive the treatment effectively. In this case operation of the moving element 50 and adjustment of the height of the earth electrode 27' can be attained without any danger even after the high voltage generating device 16 is rendered "ON" condition, because the element 50 and the electrode 27' are earthed. When the position of the earth electrode 27' is properly adjusted to change the distance from the main electrode 3, there can be changed the intensity of the electric field formed between both of the electrodes even if the voltage generated by the device 16 is held at a certain value. Therefore, adjustment of the position of the earth electrode 27' can attain same function as that attained by changing the voltage generated by the device 16.

It may be desirable that the earth electrode 27' is exchanged with a new one depending on that part of the body which is to receive the treatment. For example, in the case of treating the knee of the patient, there may be used an earth electrode 27a shown in FIG. 18. This earth electrode 27a can be easily attached to the supporting rod 53 by screwing its screw 57 into the tapped hole 56 of the supporting rod 53.

What is claimed is:

1. A therapeutical apparatus using electric field comprising a main electrode arranged at the head end of a support surface on which a patient lies, a further electrode arranged at the foot end of said support surface, insulated conductors, connected to the respective electrodes, for enabling a voltage having an AC component to be applied to the electrodes, a monitoring means for enabling monitoring of the continuity of an electrical circuit formed by said main electrode and the said conductors connected thereto when a voltage is applied to said main electrode, said monitoring means being disposed adjacent to the main electrode and being connected in a circuit which includes said electrodes and which is completed through the body of the patient when the patient contacts the further electrode and said monitoring means, said monitoring means comprising a conductive plate and an insulating plate connected to the face of the conductive plate and adapted to be contacted by the patient, and a detecting means, operative respective to the monitoring means being touched by the patient, arranged between the conductive plate and the main electrode, said detecting means comprising an indicator device which is energized when a said voltage is being applied to said main electrode and which is not energized when a voltage is not being applied to said main electrode to thereby enable faults to be detected in the said circuit formed by the main electrode and the conductors.

2. A therapeutical apparatus according to claim 1 wherein the main electrode is detachable from the apparatus and is housed in a casing attached to the upper portion of an L-shaped supporting frame, said supporting frame including horizontal portion adapted to be inserted under a mat disposed on the supporting surface on which the patient lies.

3. A therapeutical apparatus according to claim 1 wherein one of the electrodes is insulatingly supported in a housing arranged at the head end of a supporting surface on which the patient lies, a mat being laid under the patient on the bed.

4. A therapeutical apparatus according to claim 4 further comprising mounting means for movably mounting the electrode provided at the head end of the support surface, said mounting means including a pair of spaced, parallel wall plates and a movable support member for mounting the said electrode for movement along the upper edges of said wall plates, and including a pair of grooved wheels which ride on the upper edges of the wall plates.

* * * * *